United States Patent [19]

Yamamoto et al.

[11] 4,186,152
[45] Jan. 29, 1980

[54] OXIDATION OF OLEFINS

[75] Inventors: Haruhisa Yamamoto; Shinichi Akiyama, both of Takaoka, Japan

[73] Assignee: Nippon Zeon Co., Ltd., Tokyo, Japan

[21] Appl. No.: 821,315

[22] Filed: Aug. 2, 1977

[30] Foreign Application Priority Data

Aug. 6, 1976 [JP] Japan .................................. 51-93661

[51] Int. Cl.² .............................................. C07C 45/04
[52] U.S. Cl. .................................................. 260/604 R
[58] Field of Search ...................... 260/604 R; 252/432

[56] References Cited

U.S. PATENT DOCUMENTS

| 2,799,978 | 7/1957 | Ohara | 260/604 R |
| 3,679,603 | 7/1972 | Garnish et al. | 252/432 |
| 3,716,496 | 2/1973 | Yoshino | 260/533 N |

FOREIGN PATENT DOCUMENTS

| 47-32043 | 9/1972 | Japan | 260/604 R |
| 47-32044 | 9/1972 | Japan | 260/604 R |
| 48-172353 | 5/1973 | Japan | 260/604 R |
| 1390271 | 4/1975 | United Kingdom | 260/604 R |

Primary Examiner—Werren B. Lone

Attorney, Agent, or Firm—Wenderoth, Lind & Ponack

[57] ABSTRACT

A catalyst for oxidation of olefins which has a composition of the general formula $$Mo_aBi_bFe_cCo_dNi_eBe_fQ_gR_hX_iO_j$$

wherein Q is at least one element selected from K, Rb, Cs and Tl; R is at least one element selected from P, As and B; X is at least one element selected from Ce, Ti, Te, Zn, Ge, Sn, Cr, Ga, La, In, Al, Cd, Pd, Mn, V, Pb, Nb, Ag, Zr, Cu, Nd and U; a, b, c, d, e, f, g, h and i respectively represent the numbers of Mo, Bi, Fe, Co, Ni, Be, Q, R and X atoms, and when a is 12, b is 0.1–10, c is 0.5–40, d is 0–12. e is 0–12 with the proviso that the sum of d and e is 0.5–15, f is 0.1–35, g is 0.01–5, h is 0–5, i is 0–12; and j is the number of oxygen atoms which satisfies the atomic valences of the other elements.

Unsaturated aldehydes can be prepared in a high selectivity and a high one-pass yield by oxidizing olefins containing 3 carbon atoms in the straight chain in the vapor phase in the presence of the aforesaid catalyst at a temperature of 250° to 700° C.

4 Claims, No Drawings

OXIDATION OF OLEFINS

This invention relates to a catalyst for oxidation of olefins, and a process for producing unsaturated aldehydes by oxidizing olefins in the presence of the aforesaid catalyst.

Some of the terms used in the present application are defined as follows:

The "olefins" denote olefins containing 3 carbon atoms in the straight chain, such as propylene, isobutylene and isoamylene.

The "first-stage oxidation" denotes the catalytic vapor-phase reaction of olefins with molecular oxygen at high temperatures in the presence of a catalyst to form the corresponding unsaturated aldehydes.

The "second-stage oxidation" denotes the catalytic vapor-phase reaction of the unsaturated aldehydes with molecular oxygen at high temperatures in the presence of a catalyst to form the corresponding unsaturated carboxylic acids.

The "continuous first stage-second stage method" denotes a method for producing unsaturated carboxylic acids from olefins by feeding the gaseous reaction mixture formed in the first-stage oxidation directly to a second-stage oxidation zone to perform the second-stage oxidation.

The "catalyst for oxidation of olefins", or the "catalyst for the first-stage oxidation" denotes a catalyst which is used in the first-stage oxidation.

The "catalyst for the second-stage oxidation" denotes a catalyst which is used in the second-stage oxidation.

It is known to produce unsaturated aldehydes such as acrolein and methacrolein by oxidizing the corresponding olefins such as propylene and isobutylene, and to produce unsaturated carboxylic acids such as acrylic acid and methacrylic acid by oxidizing the corresponding unsaturated aldehydes. Known prior techniques for the production of unsaturated carboxylic acids from the corresponding olefins include a method which comprises separating an unsaturated aldehyde from the reaction mixture obtained by the first-stage oxidation, and after purifying it, submitting it to a second-stage oxidation, and a method which involves performing the first-stage oxidation and the second-stage oxidation successively without working up the first-stage reaction mixture (British Pat. No. 939,713). The latter is considered to be commercially advantageous because it does not require a treating step such as the separation and purification of the unsaturated aldehyde, and therefore has advantages in apparatus, operation and economy.

However, the continuous first stage-second stage method generally gives far inferior results to the case of independently performing the second-stage oxidation using the purified unsaturated aldehyde as a starting material. This tendency is especially outstanding in the production of methacrylic acid from isobutylene. For this reason, no suggestion has been made so far which would make possible the commercial production of methacrylic acid by the continuous first stage-second stage method.

The underlying difficulties are believed to be the formation of by-product impurities and the remaining of unreacted isobutylene in the first-stage oxidation. The present inventors carefully studied these difficulties, and found that the reaction mixture obtained by the first-stage oxidation contains unsaturated hydrocarbons such as diisobutylene, benzene, toluene, xylene and ethylbenzene in addition to the unreacted isobutylene and a tar-like by-product, and the presence of these hydrocarbons is a main cause for the inferior reaction results in the second-stage oxidation.

In the production of methacrylic acid from isbutylene by the continuous first stage-second stage method, it is desired to develop a novel oxidation catalyst that simultaneously meets the following two requirements which seem to be inconsistent with each other.

(1) It should afford a high conversion of isobutylene and thus reduce the amount of the unreacted isobutylene.

(2) It should reduce the formation of not only a tar-like by-product but also unsaturated hydrocarbons such as diisobutylene, benzene, toluene, xylene and ethylbenzene.

In addition to these requirements, such a catalyst should also meet normal requirements for industrial catalysts such as a high selectivity to MAL (which is associated with a high one-pass yield), and a long active lifetime.

Accordingly, it is an object of this invention to provide a novel catalyst for oxidation of olefins, which can afford unsaturated aldehydes from olefins in a high selectivity and a high one-pass yield, and has a long active lifetime.

Another object of this invention is to provide a novel catalyst for oxidation of olefins which meets the two requirements described above.

Still another object of this invention is to provide a process for preparing unsaturated aldehydes in a high selectivity and a high yield by using such a catalyst for oxidation of olefins.

According to this invention, there is provided a catalyst which can achieve these objects, said catalyst having the composition

$Mo_aBi_bFe_cCo_dNi_eBe_fQ_gR_hX_iO_j$ wherein Q is at least one element selected from K, Rb, Cs and Tl; R is at least one element selected from P, As and B; X is at least one element selected from Ce, Ti, Te, Zn, Ge, Sn, Cr, Ga, La, In, Al, Cd, Pd, Mn, V, Pb, Nb, Ag, Zr, Cu, Nd and U; a, b, c, d, e, f, g, h and i, respectively represent the numbers of Mo, Bi, Fe, Co, Ni, Be, Q, R and X atoms, and when a is 12, b is 0.1–10, c is 0.5–40, d is 0–12, e is 0–12 with the proviso that the sum of d and e is 0.5–15, f is 0.1–35, g is 0.01–5, h is 0–5, and i is 0–12; and j is the number of oxygen atoms which satisfies the atomic valences of the other elements.

A catalyst of the above general formula in which when a is 12, b is 0.5–7, c is 1–35, d is 0–10, e is 0–10 with the proviso that the sum of d and e is 0.5–12, f is 0.1–30, g is 0.01–4, h is 0–4, and i is 0–8 is a preferred embodiment of the present invention.

A catalyst of the above general formula wherein when a is 12, b is 0.5–7, c is 8–30, d is 0–10, e is 0–10 with the proviso that the sum of d and e is 0.5–12, f is 2–20, g is 0.01–3, h is 0–3, and i is 0–8 is an especially preferred embodiment of the invention.

Although the exact structure of the catalyst of this invention is not clear, the composition of the ingredients forming the catalyst is believed to be basically expressed by the above general formula.

The use of these catalysts of the invention can afford methacrolein in a high yield and a high selectivity even when the conversion of isobutylene in its oxidation is high, and can drastically reduce the amounts of by-product unsaturated hydrocarbons such as diisobutylene, benzene, toluene, xylene or ethylbenzene. Accordingly, the catalysts of this invention are very suitable for production of methacrolein, and when used as a first-stage oxidation catalyst in the continuous first stage-second stage method, they do not substantially hamper the second-stage oxidation reaction over long periods of time. Furthermore, the catalysts of this invention can give acrolein in a high yield in the catalytic oxidation of propylene, and are very effective in the continuous first stage-second stage method for producing acrylic acid from propylene.

Such an effect of this invention can be specifically obtained by the inclusion of Be in the catalyst ingredients as shown in the above general formula. If this ingredient is not present, the activities of the catalysts are low, and the formation of by-product unsaturated hydrocarbons greatly increases. This is presumably because the presence of Be makes the structure of the active seed in the catalysts of this invention quite different from those of other known catalysts of a similar composition. For example, the X-ray diffraction pattern of a catalyst in accordance with this invention does not at all show a characteristic peak based on beryllium oxide crystals. It is presumed from this fact that beryllium oxide does not exist alone in the catalysts of this invention.

Various catalysts having a composition expressed by general formulae similar to that which expresses the catalysts of this invention have been known. But as will be shown in Comparative Examples to be given hereinbelow, catalysts which contain other elements of Group II of the periodic table (to which beryllium belongs) in place of beryllium exhibit quite different catalytic activities from the catalysts of this invention, and cannot achieve the objects of this invention.

Known catalysts having a composition similar to that of the catalysts of this invention show good performance only when the number of Fe atoms is within a very narrow range of 0.5 to 3 with the number of Mo atoms taken as 12 (for example, Japanese Patent Publication No. 17253/73). In contrast, the catalysts of this invention exhibit a high activity when the number of Fe atoms is within a broad range of 0.5 to 40, and exhibit the best performance when the number of Fe atoms is within the range of 8 to 30.

The catalysts of this invention can be prepared by various methods known in the art such as an evaporation method, an oxide mixing method and a coprecipitation method. The starting materials for the individual elements in the catalyst may be not only their oxides, but any other compounds which will constitute the catalyst of this invention by calcination. Examples of these starting materials are salts containing these elements (such as ammonium salts, nitrate salts, carbonate salts, organic acid salts, and halides), free acids, acid anhydrides, condensed acids, and heterpolyacids containing molybdenum such as phosphomolybdic acid or silicomolybdic acid, and their salts such as ammonium salts or metal salts. The use of a silicon-containing compound such as silicomolybdic acid does not adversely affect the activity of the resulting catalyst.

Calcination treatment for the purpose of catalyst preparation, catalyst activation, etc. is performed usually at 300° to 900° C., preferably 450° to 700° C. for about 4 to 16 hours. If desired, a primary calcination treatment may be performed at a temperature below the abovementioned calcination temperature before the above calcination treatment.

The catalysts of this invention can be used directly as prepared, and also as deposited on a carrier of a suitable shape, or as diluted with a carrier (diluent) in the form of powder, sol, gel, etc. Known carriers can be used for this purpose. Examples include titanium dioxide, silica gel, silica sol, diatomaceous earth, silicon carbide, alumina, pumice, silica-alumina, bentonite, zirconia, zeolite, and refractories. Silicon-containing carriers are especially suitable.

The amount of the carrier can be suitably chosen. The catalyst is made into a suitable shape such as powder or tablets, and can be used in any of a fixed bed, a moving bed, and a fluidized bed.

The catalysts of this invention are useful for oxidizing olefins having three carbon atoms in the straight chain, such as propylene, isobutylene and isoamylene, especially isobutylene. These olefins need not to be highly pure, but may contain impurities. However, when the oxidation is performed by the continuous first stage-second stage method, the inclusion of large amounts of impurities possibly containing unsaturated hydrocarbons in the reacted gas from the first-stage oxidation is undesirable. Molecular oxygen may be singly used, but for commercial operations, the use of air is practical. Furthermore, in this reaction, the molecular oxygen may be diluted with an inert gas which does not adversely affect the reaction, such as steam, nitrogen, argon or carbon dioxide gas. It is especially preferred to dilute it with steam.

In the production of unsaturated aldehydes from the corresponding olefins using the catalysts of this invention, the reaction temperature is 250° to 700° C., preferably 250° to 550° C.; the reaction pressure is normal atmospheric pressure to 10 atmospheres; the space velocity (SV) of the entire starting gases is 200 to 10000 $hr^{-1}$, preferably 300 to 6000 $hr^{-1}$ (based on STP); the olefin concentration in the fed starting gases is 0.5 to 25% by volume; and the olefin to oxygen ratio is 1:0.5–7. The preferred composition of the starting gaseous mixture is olefin:air:steam=1:3–30:5–90 (molar ratio).

The reaction conditions in the first-stage oxidation in the continuous first stage-second stage method can be easily determined experimentally if a catalyst for the second-stage oxidation is set. Hence, the reaction conditions for the first-stage oxidation cannot be definitely fixed. Usually, however, the reaction temperature is 250° to 700° C., preferably 250° to 550° C.; the reaction pressure is normal atmospheric pressure to 10 atmospheres; the space velocity of the entire starting gases is 200 to 10000 $hr^{-1}$, preferably 300 to 4000 $hr^{-1}$; the olefin concentration is 0.5 to 10% by volume, preferably 0.5 to 8% by volume; the olefin to oxygen ratio is 1:1.5–7; and the preferred composition of the gaseous mixture is olefin:air:steam=1:7.5–30:5–90 (molar ratio).

For the second-stage oxidation in the continuous first stage-second stage method, any known catalysts can be used. Examples include P-Mo-R (R is at least one of Tl, alkali metals and alkaline earth metals) type oxidation catalysts; oxidation catalysts having compositions resulting from incorporating the above P-Mo-R type oxidation catalysts with at least one element selected from Si, Cr, Al, Ge, Ti, V, W, Bi, Nb, B, Ga, Pb, Sn, Co, Pd, As, Zr, Sb, Te, Fe, Ni, In, Cu, Ag, Mn, La, Nb, Ta and Sm; P-Mo-As type oxidation catalysts; P-Mo-As-alkali metal type oxidation catalysts; oxidation catalysts having compositions resulting from the incorporation of the P-Mo-As-alkali metal type catalysts with at least one element selected from V, W, Cu, Fe, Mn and Sn; P-Mo-Sb type oxidation catalysts; oxidation catalysts having compositions resulting from the incorporation of the P-Mo-Sb type catalysts with at least one element selected from W, Fe, Co, V, Al, Pb, Cr, Sn, Bi, Cu, Ni, Mg, Ca, Ba and Zn; P-Mo-Pd type oxidation catalysts; P-Pd-Sb type oxidation catalysts; oxidation catalysts having compositions resulting from the incorporation of the P-Pd-Sb type catalysts with at least one element selected from Bi, Pb, Cr, Fe, Ni, Co, Mn, Sn, U and Ba; and oxidation catalysts having compositions resulting from the incorporation of the aforementioned oxidation catalysts with ammonium.

The second-stage oxidation is performed under substantially the same reaction conditions as in the first-stage oxidation, but as described above, specific conditions are selected according to the catalyst used. Preferably, the first-stage reaction mixture obtained under the aforesaid reaction conditions is directly offered as a starting material in the second-stage oxidation, and reacted under conditions suitable for the catalyst used.

The following examples specifically illustrate the present invention. In these examples, the conversion, selectivity and one-pass yield are calculated in accordance with the following equations. All analyses were made by gas chromatography. For simplicity, the indication of oxygen in the catalyst composition is omitted.

In the following description, i-B stands for isobutylene; MAL for methacrolein: and MAA for methacrylic acid. The reaction results obtained by using propylene instead of isobutylene can be calculated by substituting propylene for i-B, acrolein for MAL, and acrylic acid for MAS in the following equations. [Calculating equations for the results of the first-stage oxidation]

$$\text{i-B conversion (\%)} = \frac{\text{Reacted i-B (moles)}}{\text{Fed i-B (moles)}} \times 100$$

Percentage of unsaturated hydrocarbons =

$$\left[ \frac{\text{Unreacted i-B (moles)}}{\text{Fed i-B (moles)}} + \frac{\text{Formed diisobutylene (based on carbon)}}{\text{Fed i-B (based on carbon)}} + \right.$$

$$\frac{\text{Formed benzene (based on carbon)}}{\text{Fed i-B (based on carbon)}} +$$

$$\frac{\text{Formed toluene (based on carbon)}}{\text{Fed i-B (based on carbon)}} +$$

$$\frac{\text{Formed xylene (based on carbon)}}{\text{Fed i-B (based on carbon)}} +$$

$$\left. \frac{\text{Formed ethylbenzene (based on carbon)}}{\text{Fed i-B (based on carbon)}} \right] \times 100$$

$$\text{One-pass yield of MAL (\%)} = \frac{\text{Formed MAL (moles)}}{\text{Fed i-B (moles)}} \times 100$$

$$\text{Selectivity of MAL (\%)} = \frac{\text{Formed MAL (moles)}}{\text{Reacted i-B (moles)}} \times 100$$

[Calculating equations for the results of the second-stage oxidation]

$$\text{MAL conversion (\%)} = \frac{\text{Reacted MAL (moles)}}{\text{Fed MAL (moles)}} \times 100$$

$$\text{One-pass yield of MAA (based on MAL) (\%)} = \frac{\text{Formed MAA (moles)}}{\text{Fed MAL (moles)}} \times 100$$

$$\text{Selectivity of MAA (based on MAL) (\%)} = \frac{\text{Formed MAA (moles)}}{\text{Reacted MAL (moles)}} \times 100$$

Conversion of unsaturated hydrocarbons (%) =

$$\frac{\text{Reacted unsaturated hydrocarbons (based on carbon)}}{\text{Fed unsaturated hydrocarbons (based on carbon)}} \times 100$$

One-pass yield of MAA (based on i-B) (%) =

-continued $$\frac{\text{Formed MAA (moles)}}{\text{i-B fed to the first-stage oxidation zone (moles)}} \times 100$$

EXAMPLE 1

A. Preparation of catalyst

Bismuth nitrate (48.5 g), 116.5 g of cobalt nitrate, 29.1 g of nickel nitrate, 484.8 g of ferric nitrate, 56.1 g of beryllium nitrate and 10.1 g of potassium nitrate were added to 150 ml of water and dissolved under heat to form a solution (solution A). Ammonium molybdate (212 g) was dissolved in 400 ml of water by heating, and 5.76 g of 85% phosphoric acid was added to form a solution (solution B). Solution B was added to solution A which was stirred at an elevated temperature. With thorough stirring, the mixture was evaporated to dryness, and dried at 120° C. for 8 hours. Then, the dried mixture was calcined at 600° C. for 16 hours in a muffle furnace. The resulting solid was pulverized and sieved to form particles having a size of 4 to 8 mesh. The composition of the resulting catalyst was as follows:

$$Mo_{12}Bi_1Fe_{12}Co_4Ni_1Be_3P_{0.5}K_1$$

B. Reaction procedure

The reaction was perfomred by the continuous first stage-second stage method in the following manner.

(1) First-stage oxidation reaction 100 ml of the catalyst obtained was filled into a stainless steel reaction tube having an inside diameter of 2.5 cm and a length of 60 cm, and heated over a metal bath. A starting gaseous mixture of isobutylene, air and steam in a mole ratio of 4:55:41 was passed through the catalyst layer at a space velocity of 2000 hr$^{-1}$.

(2) Second-stage oxidation reaction

As a catalyst for the second-stage oxidation, 100 ml of the Mo-P-Cs-Cr catalyst disclosed in Example 1 of the specification of Japanese Patent Publication No. 10846/75 [Mo:P:Cs:Cr=1:0.16:0.16:0.16 (atomic ratio); calcined at 450° C.; catalyst particle diameter 4–8 mesh] was filled into a stainless steel reaction tube having an inside diameter of 2.5 cm and a length of 60 cm, and heated over a metal bath. The reacted gas obtained by the first-stage oxidation was directly passed through the catalyst layer.

The results obtained in the first-stage oxidation and the second-stage oxidation are shown in Table 1. In Table 1, the reaction temperatures refer to those of the metal bath which were maintained constant (the same will apply hereinbelow).

EXAMPLES 2 TO 12

First-stage oxidation catalysts were prepared by the same procedure as in Example 1 except that the composition of the catalyst of Example 1 was varied. Using these catalysts, the same continuous first stage-second stage reaction as in Example 1 was performed at varying reaction temperatures.

The reaction temperatures, the catalyst compositions and the results are shown in Table 1.

Comparative Examples 1 to 4

The catalyst disclosed in Example 1 of the specification of Japanese Patent Publication No. 32044/72 (Comparative Example 1), the catalyst disclosed in Example 1 of the specification of Japanese Patent Publication No. 32043/72 (Comparative Example 2), the catalyst disclosed in Example 3 of the specification of Japanese Patent Publication No. 42813/72 (Comparative Example 3), and the catalyst disclosed in Example 1 of the specification of Japanese Patent Publication No. 17253/73 (Comparative Example 4) were prepared (the catalyst particle sizes were 4 to 8 mesh) by the methods described in these specifications. Using these catalysts, the same continuous first stage-second stage reaction as in Example 1 was performed. The results are shown in Table 2.

Comparative Examples 5 and 6

The same catalysts as in Examples 2 and 5 except that they did not contain Be were prepared, and using these catalysts, the same continuous first stage-second stage reactions as in Examples 2 and 5 were performed. The results are shown in Table 2.

The results in Tables 1 and 2 show that the presence of Be brings about good results not only in the first-stage oxidation reaction, but also in the second-stage oxidation reaction.

Comparative Examples 7 to 16

Catalysts shown in Table 2 (Comparative Examples 7 to 10) were prepared by the same procedure as in Example 1 except that 76.9 g of magnesium nitrate, 70.8 g of calcium nitrate, 63.5 g of strontium nitrate and 78.4 g of barium nitrate were respectively used instead of 56.1 g of beryllium nitrate. Similarly, comparative catalysts (Comparative Examples 11 and 12) corresponding to the catalyst of the invention used in Example 8, and comparative catalysts (Comparative Examples 13 to 16) corresponding to the catalyst of this invention used in Example 11 were prepared. The same reaction as in Example 1 was carried out using these catalysts in the first-stage oxidation catalyst. The results obtained are shown in Table 2.

It is apparent from a comparison of these comparison catalysts with the catalysts of this invention that catalysts containing Mg, Ca, Sr and Ba (which are alkaline earth meal metals) instead of Be give very poor reaction results when used as first-stage oxidation catalysts. Furthermore, when they are used as first-stage oxidation catalysts in the continuous first stage-second stage method, the amounts of the unreacted isobutene and of by-product unsaturated hydrocarbons formed are both large. Hence, the second-stage oxidation reaction runs out of control, and the second-stage oxidation catalysts lose activity within short periods of time.

Table 1

| | Results of the first-stage oxidation | | | | | | | | | | | |
|---|---|---|---|---|---|---|---|---|---|---|---|---|
| | Catalyst composition (atomic ratio) | | | | | | | | Reaction temperature (°C.) | i-B conversion (%) | Proportion of unsaturated hydrocarbons formed (%) | MAL | |
| Example | Mo | Bi | Fe | Co | Ni | Be | P | K | | | | One-pass yield (%) | Selectivity (%) |
| 1 | 12 | 1 | 12 | 4 | 1 | 3 | 0.5 | 1 | 340 | 97.6 | 2.9 | 78.0 | 79.9 |
| 2 | 12 | 1 | 6 | 4 | 1 | 3 | 0.5 | 1 | 370 | 97.0 | 4.0 | 75.8 | 78.1 |
| 3 | 12 | 1 | 18 | 4 | 1 | 3 | 0.5 | 1 | 345 | 97.3 | 3.3 | 79.2 | 81.4 |
| 4 | 12 | 1 | 30 | 4 | 1 | 3 | 0.5 | 1 | 360 | 96.7 | 4.1 | 78.1 | 80.8 |
| 5 | 12 | 1 | 4 | 4 | 1 | 3 | 0.5 | 1 | 365 | 96.5 | 4.2 | 75.6 | 78.3 |
| 6 | 12 | 3 | 12 | 4 | 1 | 3 | — | 0.75 | 340 | 97.5 | 3.0 | 79.0 | 81.0 |
| 7 | 12 | 6 | 12 | 4 | 1 | 10 | 0.5 | 0.75 | 340 | 97.2 | 3.2 | 77.9 | 80.1 |
| 8 | 12 | 3 | 12 | — | 5 | 5 | 0.5 | 0.75 | 335 | 97.0 | 3.3 | 78.6 | 81.0 |
| 9 | 12 | 1 | 12 | 4 | 1 | 1 | 0.5 | 1 | 340 | 97.0 | 3.6 | 78.7 | 81.1 |
| 10 | 12 | 1 | 12 | 4 | 1 | 20 | 2 | 1.5 | 342 | 96.8 | 3.7 | 78.1 | 80.7 |
| 11 | 12 | 1 | 12 | 5 | — | 3 | 0.5 | 0.2 | 325 | 96.4 | 3.9 | 79.3 | 82.3 |
| 12 | 12 | 1 | 12 | 4 | 1 | 3 | 0.5 | 2.0 | 370 | 96.6 | 4.0 | 77.7 | 80.4 |

| | Results of the second-stage oxidation | | | | | |
|---|---|---|---|---|---|---|
| Example | Reaction temperature (°C.) | MAL conversion (%) | MAA (based on MAL) | | Conversion of unsaturated hydrocarbons (%) | One-pass yield of MAA (based on i-B) (%) |
| | | | One-pass yield (%) | Selectivity (%) | | |
| 1 | 335 | 80.8 | 60.5 | 74.9 | 100 | 47.2 |
| 2 | 335 | 75.8 | 57.1 | 75.3 | 100 | 43.3 |
| 3 | 335 | 77.0 | 58.9 | 76.5 | 100 | 46.6 |
| 4 | 335 | 76.1 | 56.8 | 74.6 | 100 | 44.4 |
| 5 | 335 | 76.4 | 56.9 | 74.5 | 100 | 43.0 |
| 6 | 335 | 77.3 | 59.6 | 77.1 | 100 | 47.1 |
| 7 | 335 | 78.4 | 60.4 | 77.0 | 100 | 47.1 |
| 8 | 335 | 77.2 | 59.3 | 76.8 | 100 | 46.6 |
| 9 | 335 | 77.1 | 59.6 | 77.3 | 100 | 46.9 |
| 10 | 335 | 76.7 | 57.6 | 75.1 | 100 | 45.0 |
| 11 | 335 | 77.5 | 58.5 | 75.5 | 100 | 46.4 |
| 12 | 335 | 76.2 | 56.9 | 74.7 | 100 | 44.2 |

Table 2

| Comparative example | Composition (atomic ratio) of the first-stage oxidation catalyst | | | | | | | | | | | | |
|---|---|---|---|---|---|---|---|---|---|---|---|---|---|
| | Mo | Bi | Fe | Co | Ni | P | K | Tl | Si | Mg | Ca | Sr | Ba |
| 1 | 12 | 1 | 1 | 4 | 4.5 | 0.1 | — | 0.4 | — | — | — | — | — |
| 2 | 12 | 1 | 1 | — | 8.5 | 0.1 | — | 0.4 | — | — | — | — | — |

Table 2-continued

| | | | | | | | | | | | | | |
|---|---|---|---|---|---|---|---|---|---|---|---|---|---|
| 3 | 12 | 1 | 1 | 4 | — | — | 0.08 | — | 1.5 | — | — | — | — |
| 4 | 12 | 1 | 3 | 4.5 | 2.5 | 0.5 | 0.07 | — | — | — | — | — | — |
| 5 | 12 | 1 | 6 | 4 | 1 | 0.5 | 1 | — | — | — | — | — | — |
| 6 | 12 | 1 | 4 | 4 | 1 | 0.5 | 1 | — | — | — | — | — | — |
| 7 | 12 | 1 | 12 | 4 | 1 | 0.5 | 1 | — | — | 3 | — | — | — |
| 8 | 12 | 1 | 12 | 4 | 1 | 0.5 | 1 | — | — | — | 3 | — | — |
| 9 | 12 | 1 | 12 | 4 | 1 | 0.5 | 1 | — | — | — | — | 3 | — |
| 10 | 12 | 1 | 12 | 4 | 1 | 0.5 | 1 | — | — | — | — | — | 3 |
| 11 | 12 | 3 | 12 | — | 5 | 0.5 | 0.75 | — | — | 5 | — | — | — |
| 12 | 12 | 3 | 12 | — | 5 | 0.5 | 0.75 | — | — | — | — | — | 5 |
| 13 | 12 | 1 | 12 | 5 | — | 0.5 | 0.2 | — | — | 3 | — | — | — |
| 14 | 12 | 1 | 12 | 5 | — | 0.5 | 0.2 | — | — | — | 3 | — | — |
| 15 | 12 | 1 | 12 | 5 | — | 0.5 | 0.2 | — | — | — | — | 3 | — |
| 16 | 12 | 1 | 12 | 5 | — | 0.5 | 0.2 | — | — | — | — | — | 3 |

Results of the first-stage oxidation

| Comparative example | Reaction temperature (°C.) | i-B conversion (%) | Proportion of unsaturated hydrocarbons formed (%) | MAL One-pass yield (%) | MAL Selectivity (%) |
|---|---|---|---|---|---|
| 1 | 340 | 94.1 | 9.1 | 60.8 | 64.6 |
| 2 | 340 | 96.4 | 9.6 | 59.8 | 62.0 |
| 3 | 340 | 95.3 | 8.6 | 62.2 | 65.3 |
| 4 | 340 | 90.0 | 13.0 | 57.7 | 64.1 |
| 5 | 370 | 94.9 | 10.3 | 60.4 | 63.7 |
| 6 | 365 | 88.6 | 14.6 | 59.5 | 67.2 |
| 7 | 340 | 58.3 | 44.7 | 45.5 | 78.0 |
| 8 | 340 | 56.0 | 46.7 | 44.5 | 79.5 |
| 9 | 340 | 49.5 | 52.8 | 39.6 | 80.0 |
| 10 | 340 | 42.3 | 59.8 | 33.5 | 79.2 |
| 11 | 335 | 45.7 | 56.4 | 36.8 | 80.5 |
| 12 | 335 | 40.0 | 62.0 | 32.0 | 80.0 |
| 13 | 325 | 57.5 | 45.0 | 46.1 | 80.2 |
| 14 | 325 | 55.1 | 47.1 | 43.8 | 79.5 |
| 15 | 325 | 45.3 | 56.9 | 36.1 | 79.7 |
| 16 | 325 | 41.7 | 60.4 | 33.8 | 81.1 |

Results of the second-stage oxidation

| Comparative example | Reaction temperature (°C.) | MAL conversion (%) | MAA (based on MAL) One-pass yield (%) | MAA (based on MAL) Selectivity (%) | Conversion of unsaturated hydrocarbons (%) | One-pass yield of MAA (based on i-B) (%) |
|---|---|---|---|---|---|---|
| 1 | 335 | 58.4 | 37.1 | 63.5 | 100 | 22.7 |
| 2 | 335 | 58.3 | 36.9 | 63.3 | 100 | 22.2 |
| 3 | 335 | 60.4 | 37.4 | 61.9 | 100 | 23.3 |
| 4 | 335 | 50.4 | 30.2 | 59.9 | 100 | 17.6 |
| 5 | 335 | 61.4 | 39.3 | 64.0 | 100 | 23.7 |
| 6 | 335 | 52.6 | 32.2 | 61.2 | 100 | 19.2 |
| 7 | 355 | | | | | |
| 8 | 355 | | | | | |
| 9 | 355 | | | | | |
| 10 | 355 | The reaction ran out of control, and MAA was scarcely formed. | | | | |
| 11 | 355 | | | | | |
| 12 | 355 | | | | | |
| 13 | 355 | | | | | |
| 14 | 355 | | | | | |
| 15 | 355 | | | | | |
| 16 | 355 | | | | | |

REFERENTIAL EXAMPLES 1 TO 7

With regard to the second-stage oxidation catalyst used in Example 1, the effect of unsaturated hydrocarbons contained in the feed gas for the second-stage oxidation reaction on the results of reaction was examined.

Instead of the reacted gas in the first stage oxidation, a gaseous mixture obtained by adding isobutylene or xylene in the concentrations shown in Table 3 to MAL (purity 99.5% by weight) was reacted by the same procedure as in Example 1 at a space velocity of 2000 hr$^{-1}$ while maintaining the MAL (a mixture containing isobutylene or xylene):$O_2$:$N_2$:$H_2O$ mole ratio at 1:1.5:13.0:17.5. The results are shown in Table 3.

It can be seen from Table 3 that in the second-stage oxidation reaction, unsaturated hydrocarbons such as isobutylene or xylene adversely affect the formation of MAA.

Table 3

| Referential Example | Concentration of unsaturated hydrocarbon in fed MAL (%, based on carbon) Isobutylene | Concentration of unsaturated hydrocarbon in fed MAL (%, based on carbon) Xylene | Reaction temperature (°C.) | Conversion of MAL (%) | One-pass yield (%) | Selectivity (%) |
|---|---|---|---|---|---|---|
| 1 | 0 | 0 | 335 | 81.1 | 62.8 | 77.4 |
| 2 | 5 | 0 | 335 | 77.4 | 59.1 | 76.4 |
| 3 | 10 | 0 | 335 | 63.6 | 43.8 | 68.9 |
| 4 | 15 | 0 | 335 | 54.4 | 33.7 | 62.0 |
| 5 | 0 | 1 | 335 | 76.9 | 57.9 | 75.3 |

Table 3-continued

| Referential Example | Concentration of unsaturated hydrocarbon in fed MAL (%, based on carbon) Isobutylene | Xylene | Reaction temperature (°C.) | Conversion of MAL (%) | One-pass yield (%) | Selectivity (%) |
| --- | --- | --- | --- | --- | --- | --- |
| 6 | 0 | 4 | 335 | 66.7 | 42.1 | 63.1 |
| 7 | 0 | 7 | 335 | 56.3 | 34.5 | 61.3 |

EXAMPLES 13 TO 22

By the same procedure as in Example 1, catalysts were prepared by incorporating an additional ingredient (ingredient Z) (Ce, Ti, Zn, Cr, La, Al, Cd, Pb, Ag and Cu) in the catalyst prepared in Example 1. The continuous first stage-second stage reaction was performed in the same way as in Example 1 using these catalysts. The results are shown in Table 4.

EXAMPLES 23 TO 31

By the same procedure as in Example 1, catalysts were prepared by replacing the phosphorus component ingredient in the catalysts used prepared in Example 1 partly or wholly by arsenic or boron, or by replacing the potassium ingredient of the catalysts prepared in Example 1 partly or wholly by rubidium, cesium or thallium. The same direct continuous first stage-second stage reaction as in Example 1 was performed using these catalysts. The results are shown in Table 5.

Table 4

| | Results of the first-stage oxidation | | | | | | | | | | | | |
| --- | --- | --- | --- | --- | --- | --- | --- | --- | --- | --- | --- | --- | --- |
| Example | Catalyst composition (atomic ratio) | | | | | | | | Reaction temperature (°C.) | i-B conversion (%) | Proportion of unsaturated hydrocarbons formed (%) | MAL | |
| | Mo | Bi | Fe | Co | Ni | Be | P | K | Z | | | One-pass yield (%) | Selectivity (%) |
| 13 | 12 | 1 | 12 | 4 | 1 | 3 | 0.5 | 1 | 1(Ce) | 340 | 97.7 | 2.8 | 79.0 | 80.9 |
| 14 | 12 | 1 | 12 | 4 | 1 | 3 | 0.5 | 1 | 3(Ti) | 340 | 97.7 | 2.7 | 80.6 | 82.5 |
| 15 | 12 | 1 | 12 | 4 | 1 | 3 | 0.5 | 1 | 2(Zn) | 340 | 97.5 | 3.4 | 79.7 | 81.7 |
| 16 | 12 | 1 | 12 | 4 | 1 | 3 | 0.5 | 1 | 2(Cr) | 340 | 98.2 | 2.6 | 78.9 | 80.3 |
| 17 | 12 | 1 | 12 | 4 | 1 | 3 | 0.5 | 1 | 1(La) | 340 | 97.4 | 3.1 | 81.2 | 83.4 |
| 18 | 12 | 1 | 12 | 4 | 1 | 3 | 0.5 | 1 | 4(Al) | 340 | 97.1 | 3.3 | 81.4 | 83.8 |
| 19 | 12 | 1 | 12 | 4 | 1 | 3 | 0.5 | 1 | 2(Cd) | 340 | 97.8 | 3.1 | 79.7 | 81.5 |
| 20 | 12 | 1 | 12 | 4 | 1 | 3 | 0.5 | 1 | 1(Pb) | 340 | 98.0 | 4.1 | 80.2 | 81.8 |
| 21 | 12 | 1 | 12 | 4 | 1 | 3 | 0.5 | 1 | 2(Ag) | 340 | 97.7 | 2.7 | 79.5 | 81.4 |
| 22 | 12 | 1 | 12 | 4 | 1 | 3 | 0.5 | 1 | 1(Cu) | 340 | 97.5 | 3.2 | 80.1 | 82.2 |

| | Results of the second-stage oxidation | | | | | |
| --- | --- | --- | --- | --- | --- | --- |
| Example | Reaction temperature (°C.) | Conversion of MAL (%) | MAA (based on MAL) | | Conversion of unsaturated hydrocarbons (%) | One-pass yield of MAA (based on i-B) (%) |
| | | | One-pass yield (%) | Selectivity (%) | | |
| 13 | 335 | 81.2 | 61.8 | 76.1 | 100 | 48.8 |
| 14 | 335 | 78.3 | 59.5 | 76.0 | 100 | 48.0 |
| 15 | 335 | 79.6 | 59.9 | 75.3 | 100 | 47.7 |
| 16 | 335 | 79.0 | 61.1 | 77.3 | 100 | 48.2 |
| 17 | 335 | 80.1 | 62.1 | 77.5 | 100 | 50.4 |
| 18 | 335 | 77.8 | 59.8 | 76.9 | 100 | 48.7 |
| 19 | 335 | 78.0 | 60.0 | 76.9 | 100 | 47.8 |
| 20 | 335 | 77.3 | 59.4 | 76.8 | 100 | 47.6 |
| 21 | 335 | 79.0 | 60.4 | 76.5 | 100 | 48.0 |
| 22 | 355 | 77.9 | 59.9 | 76.9 | 100 | 48.0 |

Table 5

| Example | Composition (atomic ratio) of the first-stage oxidation catalyst | | | | | | | | | | | |
| --- | --- | --- | --- | --- | --- | --- | --- | --- | --- | --- | --- | --- |
| | Mo | Bi | Fe | Co | Ni | Be | P | As | B | K | Rb | Cs | Tl |
| 23 | 12 | 1 | 12 | 4 | 1 | 3 | — | — | — | 1 | — | — | — |
| 24 | 12 | 1 | 12 | 4 | 1 | 3 | — | 0.5 | — | 1 | — | — | — |
| 25 | 12 | 1 | 12 | 4 | 1 | 3 | — | — | 0.5 | 1 | — | — | — |
| 26 | 12 | 1 | 12 | 4 | 1 | 3 | 0.5 | — | — | — | — | 0.1 | — |
| 27 | 12 | 1 | 12 | 4 | 1 | 3 | 0.5 | — | — | — | — | — | 1 |
| 28 | 12 | 1 | 12 | 4 | 1 | 3 | 0.5 | — | — | — | 0.75 | — | — |
| 29 | 12 | 1 | 12 | 4 | 1 | 3 | 0.5 | — | 0.5 | 0.75 | — | — | — |
| 30 | 12 | 1 | 12 | 4 | 1 | 3 | — | 0.5 | — | — | — | — | 0.75 |
| 31 | 12 | 1 | 12 | 4 | 1 | 3 | 0.5 | — | — | 0.5 | 0.5 | — | — |

| | Results of the first-stage oxidation | | | | |
| --- | --- | --- | --- | --- | --- |
| Example | Reaction temperature (°C.) | i-B conversion (%) | Proportion of unsaturated hydrocarbons formed (%) | MAL | |
| | | | | One-pass yield (%) | Selectivity (%) |
| 23 | 340 | 96.5 | 3.7 | 78.8 | 81.7 |
| 24 | 340 | 97.0 | 3.3 | 80.2 | 82.7 |
| 25 | 340 | 97.1 | 3.1 | 78.9 | 81.3 |
| 26 | 340 | 96.7 | 3.7 | 77.6 | 80.3 |
| 27 | 340 | 96.9 | 3.4 | 79.5 | 82.0 |

Table 5-continued

| | | | | | |
|---|---|---|---|---|---|
| 28 | 340 | 97.4 | 2.9 | 79.3 | 81.4 |
| 29 | 340 | 97.0 | 3.2 | 79.2 | 81.7 |
| 30 | 340 | 97.2 | 3.1 | 79.9 | 82.2 |
| 31 | 340 | 97.1 | 3.2 | 79.7 | 82.1 |

| | | Results of the second-stage oxidation | | | |
|---|---|---|---|---|---|
| | | | MAA (based on MAL) | Conversion of | One-pass |
| Example | Reaction temperature (°C.) | MAL conversion (%) | One-pass yield (%) | Selectivity (%) | unsaturated hydrocarbons (%) | yield of MAA (based on i-B) (%) |
| 23 | 335 | 78.0 | 60.2 | 77.2 | 100 | 47.4 |
| 24 | 335 | 77.2 | 59.4 | 76.9 | 100 | 47.6 |
| 25 | 335 | 77.4 | 59.4 | 76.7 | 100 | 46.9 |
| 26 | 335 | 76.0 | 57.2 | 75.3 | 100 | 44.4 |
| 27 | 335 | 77.2 | 58.4 | 75.7 | 100 | 46.4 |
| 28 | 335 | 78.0 | 60.3 | 77.3 | 100 | 47.8 |
| 29 | 335 | 77.7 | 59.4 | 76.5 | 100 | 47.0 |
| 30 | 335 | 77.3 | 59.1 | 76.5 | 100 | 47.2 |
| 31 | 335 | 77.2 | 59.4 | 76.9 | 100 | 47.3 |

EXAMPLES 32 TO 34

The first stage-second stage reactions in Examples 1, 2 and 13 were continued for 1000 hours under the same reaction conditions. Changes in the results of reaction were examined.

During the reaction, the temperatures of the metal baths in the first and second stage oxidation zones were maintained constant. The results are shown in Table 6. As can be seen from Table 6, no substantial degradation in the reaction results in the first-stage oxidation and the second-stage oxidation even after a lapse of 1000 hours.

reaction conditions. Changes in the reaction results were examined.

During the reaction, the temperatures of the metal baths in the first-stage oxidation and the second-stage oxidation were maintained constant. The results are shown in Table 6.

It is seen from Table 6 that no substantial degradation in the reaction results of the first-stage oxidation was observed, but that with the passage of time, the results of the second-stage oxidation reaction became very poor. This degradation seems to be due mainly to the effects of unsaturated hydrocarbons contained in the reacted gas formed in the first-stage oxidation.

Table 6

| | | | Results of the first-stage oxidation | | | | |
|---|---|---|---|---|---|---|---|
| | | Reaction time which passed (hours) | Reaction temperature (°C.) | i-B conversion (%) | Proportion of unsaturated hydrocarbons formed (%) | MAL One pass yield (%) | Selectivity (%) |
| Example | 1 | 0* | 340 | 97.6 | 2.9 | 78.0 | 79.9 |
| | 32 | 1000 | 340 | 97.5 | 2.8 | 78.5 | 80.5 |
| | 2 | 0* | 370 | 97.0 | 4.0 | 75.8 | 78.1 |
| | 33 | 1000 | 370 | 97.5 | 3.6 | 76.1 | 78.1 |
| | — | 0* | 340 | 98.0 | 2.5 | 78.8 | 80.4 |
| | 34 | 1000 | 340 | 98.1 | 2.5 | 78.8 | 80.3 |
| Comparative example | 5 | 0* | 370 | 94.9 | 10.3 | 60.4 | 63.7 |
| | 17 | 1000 | 370 | 94.0 | 11.2 | 60.1 | 63.9 |

The symbol (*) denotes the early stage of reaction.

| | | | | Results of second stage oxidation | | | |
|---|---|---|---|---|---|---|---|
| | | Reaction temperature (°C.) | MAL conversion (%) | MAA (based on MAL) One-pass yield (%) | Selectivity (%) | Conversion of unsaturated hydrocarbons (%) | One-pass yield on MAA (based on i-B) (%) |
| Example | 1 | 335 | 80.0 | 60.5 | 74.9 | 100 | 47.2 |
| | 32 | 335 | 81.1 | 61.0 | 75.2 | 100 | 47.9 |
| | 2 | 335 | 75.8 | 57.1 | 75.3 | 100 | 43.3 |
| | 33 | 335 | 77.2 | 57.8 | 74.9 | 100 | 44.0 |
| | 13 | 335 | 80.5 | 61.0 | 75.8 | 100 | 48.1 |
| | 34 | 335 | 80.4 | 60.7 | 75.5 | 100 | 47.8 |
| Comparative example | 5 | 335 | 61.4 | 39.3 | 64.0 | 100 | 23.7 |
| | 17 | 335 | 49.7 | 29.0 | 58.4 | 100 | 17.4 |

COMPARATIVE EXAMPLE 17

As a comparison for Example 33, the first stage-second stage reaction performed in Comparative Example 5 was continued for 1000 hours under the same

EXAMPLES 35 TO 37

The same continuous first stage-second stage reaction as in Example 1 was performed using the same first-stage oxidation reaction as used in Examples 1, 2 and 13 and propylene instead of isobutylene. The results of reaction are shown in Table 7.

Table 7

| | Catalyst composition (atomic ratio) | | | | | | | | | Reaction temperature (°C.) | Conversion of propylene (%) | Proportion of unsaturated hydrocarbons formed (%) | Acrolein | |
|---|---|---|---|---|---|---|---|---|---|---|---|---|---|---|
| | | | | | | | | | | | | | One-pass yield (%) | Selectivity (%) |
| Example | Mo | Bi | Fe | Co | Ni | Be | P | K | Ce | | | | | |
| 35 | 12 | 1 | 12 | 4 | 1 | 3 | 0.5 | 1 | — | 355 | 98.2 | 2.0 | 84.9 | 86.5 |
| 36 | 12 | 1 | 6 | 4 | 1 | 3 | 0.5 | 1 | — | 355 | 97.3 | 2.9 | 83.6 | 85.9 |
| 37 | 12 | 1 | 12 | 4 | 1 | 3 | 0.5 | 1 | 1 | 355 | 98.6 | 1.8 | 86.1 | 87.3 |

Results of the second stage oxidation

| Example | Reaction temperature (°C.) | Conversion of acrolein (%) | Acrylic acid (based on acrolein) | | Conversion of unsaturated hydrocarbons (%) | One-pass yield of acrylic acid (based on propylene) (%) |
|---|---|---|---|---|---|---|
| | | | One-pass yield (%) | Selectivity (%) | | |
| 35 | 360 | 88.7 | 80.3 | 90.5 | 100 | 68.2 |
| 36 | 360 | 87.9 | 79.2 | 90.1 | 100 | 66.2 |
| 37 | 360 | 90.0 | 82.1 | 91.2 | 100 | 70.7 |

REFERENTIAL EXAMPLE 8

As a reference example for Examples 35 to 37, the reaction was performed under the same conditions as in the second-stage reaction in Example 1 except that acrolein having a purity of 99.6% by weight was used at a space velocity of 2000 hr$^{-1}$, and the acrolein: $O_2$:$N_2$:$H_2O$ mole ratio in the starting gaseous mixture was maintained at 1:1.5:13.0:17.5. The results are shown in Table 8.

Table 8

| Reaction temperature (°C.) | 360 |
|---|---|
| Conversion of acrolein (%) | 91.0 |
| One-pass yield (%) of acrylic acid (based on acrolein) | 82.5 |
| Selectivity (%) of acrylic acid (based on acrolein | 90.7 |

What we claim is:

1. In a process comprising the production of an unsaturated aldehyde by oxidizing propylene or isobutylene in the vapor phase at a temperature of 250° to 700° C. in the presence of a catalyst to the corresponding unsaturated aldehyde, the improvement wherein the catalyst for the said oxidation has a composition of the formula

wherein Q is at least one element selected from K, Rb, Cs and Tl; R is at least one element selected from P, As and B; X is at least one element selected from Ce, Ti, Te, Zn, Ge, Sn, Cr, Ga, La, In, Al, Cd, Pd, Mn, V, Pd, Nb, Ag, Zr, Cu, Nd and U; a, b, c, d, e, f, g, h and i respectively represent the numbers of Mo, Bi, Fe, Co, Ni, Be, Q, R and X atoms, and when a is taken as 12, b is 0.1–10, c is 0.5–40, d is 0–12, e is 0–12 with the proviso that the sum of d and e is 0.5–15, f is 0.1–35, g is 0.01–5, h is 0–5, i is 0–12; and j is the number of oxygen atoms which satisfies the atomic valences of the other elements.

2. A process according to claim 1 wherein air is used as a source of oxygen.

3. A process according to claim 1 wherein the said oxidation is carried out in the presence of an inert gas.

4. A process according to claim 1 wherein the said oxidation is carried out at a temperature of 250° to 550° C.